(12) United States Patent
McKinnon et al.

(10) Patent No.: US 8,474,300 B2
(45) Date of Patent: Jul. 2, 2013

(54) METHODS TO PROVIDE A FEATURE ON A NEEDLE

(75) Inventors: Austin Jason McKinnon, Herriman, UT (US); Edward G. Henderson, III, Salt Lake City, UT (US); S. Ray Isaacson, Roy, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 880 days.

(21) Appl. No.: 12/505,912

(22) Filed: Jul. 20, 2009

(65) Prior Publication Data

US 2011/0011149 A1   Jan. 20, 2011

(51) Int. Cl.
| | | |
|---|---|---|
| *B21D 37/10* | (2006.01) | |
| *B21D 41/00* | (2006.01) | |
| *B21C 37/30* | (2006.01) | |

(52) U.S. Cl.
USPC .................. 72/416; 72/370.13; 72/370.23

(58) Field of Classification Search
USPC ............. 72/402, 412, 399, 400, 401, 416, 72/57, 370.12, 370.13, 370.23; 29/751, 753, 29/761
See application file for complete search history.

(56) References Cited

U.S. PATENT DOCUMENTS

| | | | |
|---|---|---|---|
| 2,958,929 A | 11/1960 | Vineberg et al. | |
| 3,540,112 A | 11/1970 | Knox | |
| 4,067,224 A | 1/1978 | Birks | |
| 4,952,207 A | 8/1990 | Lemieux | |
| 4,964,854 A | 10/1990 | Luther | |
| 5,085,648 A | 2/1992 | Purdy et al. | |
| 5,099,676 A * | 3/1992 | Proto et al. ................. | 72/416 |
| 5,135,504 A | 8/1992 | McLees | |
| 5,601,536 A | 2/1997 | Crawford et al. | |
| 5,608,962 A * | 3/1997 | Colligan et al. ............. | 29/517 |
| 5,722,991 A | 3/1998 | Colligan | |
| 5,833,670 A | 11/1998 | Dillon et al. | |
| 6,004,294 A | 12/1999 | Brimhall et al. | |
| 6,012,213 A | 1/2000 | Chang et al. | |
| 6,117,108 A | 9/2000 | Woehr et al. | |
| 6,224,569 B1 | 5/2001 | Brimhall | |
| 6,287,278 B1 | 9/2001 | Woehr et al. | |
| 6,322,537 B1 | 11/2001 | Chang | |
| 6,379,333 B1 | 4/2002 | Brimhall et al. | |
| 6,443,927 B1 | 9/2002 | Cook | |
| 6,443,929 B1 | 9/2002 | Kuracina et al. | |
| 6,616,630 B1 | 9/2003 | Woehr et al. | |
| 6,629,959 B2 | 10/2003 | Kuracina et al. | |

(Continued)

FOREIGN PATENT DOCUMENTS

| | | |
|---|---|---|
| DE | 938 662 C | 2/1956 |
| EP | 0 426 377 A1 | 10/1990 |
| WO | WO 02/078771 A1 | 10/2002 |
| WO | WO 02/087666 A2 | 11/2002 |

*Primary Examiner* — Dana Ross
*Assistant Examiner* — Mohammad I Yusuf
(74) *Attorney, Agent, or Firm* — Jeanne Lukasavage; Craig Metcalf; Kirton McConkie

(57) ABSTRACT

A gripping surface is provided on an outer surface of a needle shield as incorporated into an intravenous catheter assembly. The gripping surface provides a gripping position nearer the catheter adapter, catheter and needle tip for improved balance and control of the catheter assembly during insertion of the catheter. Additionally, the gripping surfaces include a guard feature to prevent a user's unintended contact with various components of the catheter assembly whereby the contact may result in an undesirable "over the bevel" condition.

9 Claims, 4 Drawing Sheets

U.S. PATENT DOCUMENTS

| | | |
|---|---|---|
| 6,652,486 B2 | 11/2003 | Bialecki et al. |
| 6,652,490 B2 | 11/2003 | Howell |
| 6,663,592 B2 | 12/2003 | Rhad et al. |
| 6,692,471 B2 | 2/2004 | Boudreaux |
| 6,761,706 B2 | 7/2004 | Vaillancourt |
| 6,860,871 B2 | 3/2005 | Kuracina et al. |
| 6,914,212 B2 | 7/2005 | Adams |
| 7,002,098 B2 | 2/2006 | Adams |
| 7,160,269 B2 | 1/2007 | Woehr |
| 7,186,239 B2 | 3/2007 | Woehr |
| 7,214,208 B2 | 5/2007 | Vaillancourt |
| 7,238,169 B2 | 7/2007 | Takagi et al. |
| 7,264,613 B2 | 9/2007 | Woehr et al. |
| 7,762,804 B1 * | 7/2010 | Stupecky ............... 425/392 |
| 2005/0027263 A1 | 2/2005 | Woehr et al. |
| 2005/0080378 A1 | 4/2005 | Cindrich et al. |
| 2006/0116638 A1 | 6/2006 | Woehr et al. |
| 2006/0270980 A1 | 11/2006 | Menzi et al. |
| 2007/0100297 A1 | 5/2007 | Woehr et al. |
| 2007/0129689 A1 | 6/2007 | Woehr et al. |
| 2007/0156093 A1 | 7/2007 | Woehr |
| 2007/0179446 A1 | 8/2007 | Carrez et al. |
| 2007/0179447 A1 | 8/2007 | Carrez et al. |
| 2008/0119876 A1 * | 5/2008 | Price et al. ............. 606/144 |

* cited by examiner

METHODS TO PROVIDE A FEATURE ON A NEEDLE

BACKGROUND OF THE INVENTION

The current invention relates to infusion devices, such as intravenous needles, used in combination with over-the-needle peripheral intravenous (IV) catheters. Specifically, the present invention relates to methods configured to provide a feature on an outer surface of a needle while generally preserving the cross-sectioned profile of the inner surface of the needle.

Intravenous (IV) needles are commonly used for a variety of infusion therapies. IV needles are commonly used in combination with an over-the-needle peripheral IV catheter. As its name implies, an over-the-needle catheter is mounted over an IV needle (i.e. an introducer needle) having a sharp distal tip. A portion of the outer surface of the needle is commonly crimped or otherwise modified to provide a feature on the needle, as shown in the PRIOR ART of FIG. 1. In FIG. 1, a portion of a needle 10 is crimped between an upper anvil 20 and a lower anvil 22. Opposing, planar surfaces 30 and 32 contact a portion of the outer surface 12 of the needle 10 and inwardly compresses or pinches the needle 10 thereby providing feature 30. Feature 30 generally comprises an outwardly extended portion of the outer surface 12 of the needle 10. The outer surface 12 of the needle 10 is extended outwardly as the upper and lower anvils 20 and 22 pinch the needle 10 resulting in a partial occlusion of a cross-section of the inner lumen 14 of the needle 10. While the PRIOR ART method provides a feature 30 on the outer surface 12 of the needle 10, the inner lumen 14 of the needle 10 is partially or completely occluded resulting in decreased flow efficiency through the needle 10.

Thus, while methods exist for providing a feature on a needle, challenges still exist. Accordingly, there is a need in the art for a method that permits the creation of a feature on an outer surface of a needle while preserving a flow efficiency through the needle. Such a method is disclosed herein.

BRIEF SUMMARY OF THE INVENTION

In order to overcome the limitations discussed above, the present invention relates to various methods for providing a needle feature on an outer surface of a needle while generally preserving the cross-sectional shape of the needle's inner lumen. Furthermore, some methods of the present invention provide a needle feature on an outer surface of a needle while preserving a flow efficiency through the needle.

Some methods of the current invention entail crimping a portion of an outer surface of a needle by compressing the portion of the needle between an upper anvil and a lower anvil. The upper and lower anvils include opposing recessed surfaces that are configured to receive upper and lower portion of the outer surface of the needle. As such, the process of compressing the needle between the upper and lower anvils prevents or limits contact between the outer surface of the needle and the recessed surfaces. The result is that the upper and lower portions of the outer surface of the needle are not affected by the crimping or compression of the upper and lower anvils.

However, in some embodiments the width of the recessed surfaces is configured to be less than the outer diameter of the needle. As such, when the needle is compressed between the upper and lower anvils, a planar surface of the anvils contacts a side portion of the outer surface of the needle. This contact between the anvils and the outer surface of the needle plastically deforms the side portion of the needle to provide a needle feature. In some embodiments, the depth and width of the recessed surfaces is configured such that the anvils contact only the outer surface of the needle and do not disturb the cross-sectional profile of the inner lumen of the needle. Thus, the methods of the current invention provide external needle features without compromising a flow efficiency through the inner lumen of the needle.

In other methods of the present invention, a stylet or mandrel is inserted into the inner lumen of the needle prior to compressing the needle between the opposing anvils. The mandrel generally includes a cross-sectional profile that is the same as the cross-sectional profile of the inner lumen. The mandrel is positioned within the inner lumen so as to overlap the portion of the needle that is compressed or crimped by the opposing anvils. The presence of the mandrel prevents plastic deformation of the inner lumen cross-sectional profile thereby ensuring that a flow efficiency of the needle is preserved. In some embodiments, a lubricant is applied to the outer surface of the mandrel prior to insertion of the mandrel within the inner lumen. In other embodiments, a lubricant is applied to the surface of the inner lumen prior to insertion of the mandrel therein.

Finally, in some methods of the present invention the contact surfaces of the opposing anvils is configured to divot the outer surface of the needle. The contact surfaces of the opposing anvils may be configured to provide a variety of needle features. For example, the contact surfaces of the opposing anvils may be configured to provide a protruding feature, a recessed feature, a spiral feature, a set of alternating features, a textured feature, and combinations thereof. Additionally, the contact surfaces of the opposing anvils may be configured to provide a series of features having a plurality of dimensions, textures, shapes, and patterns, as determined useful by a user. The current methods may also be modified to work in conjunction with other components of a catheter assembly. For example, the needle feature may be configured for use in conjunction with a safety feature of a needle housing. The needle feature may also be configured to enable controlled passage of fluids between the outer surface of the needle and a catheter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
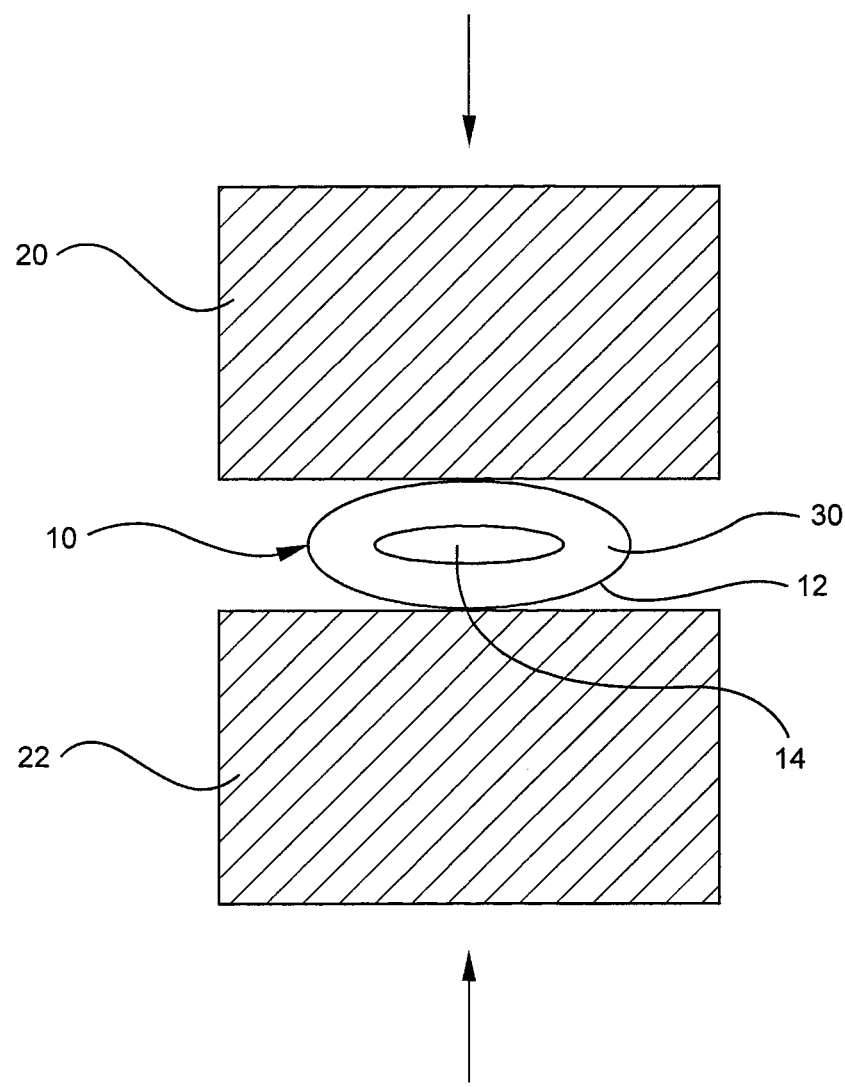
FIG. 1 is a perspective view of a PRIOR ART method for crimping a needle.
Figure 2A:
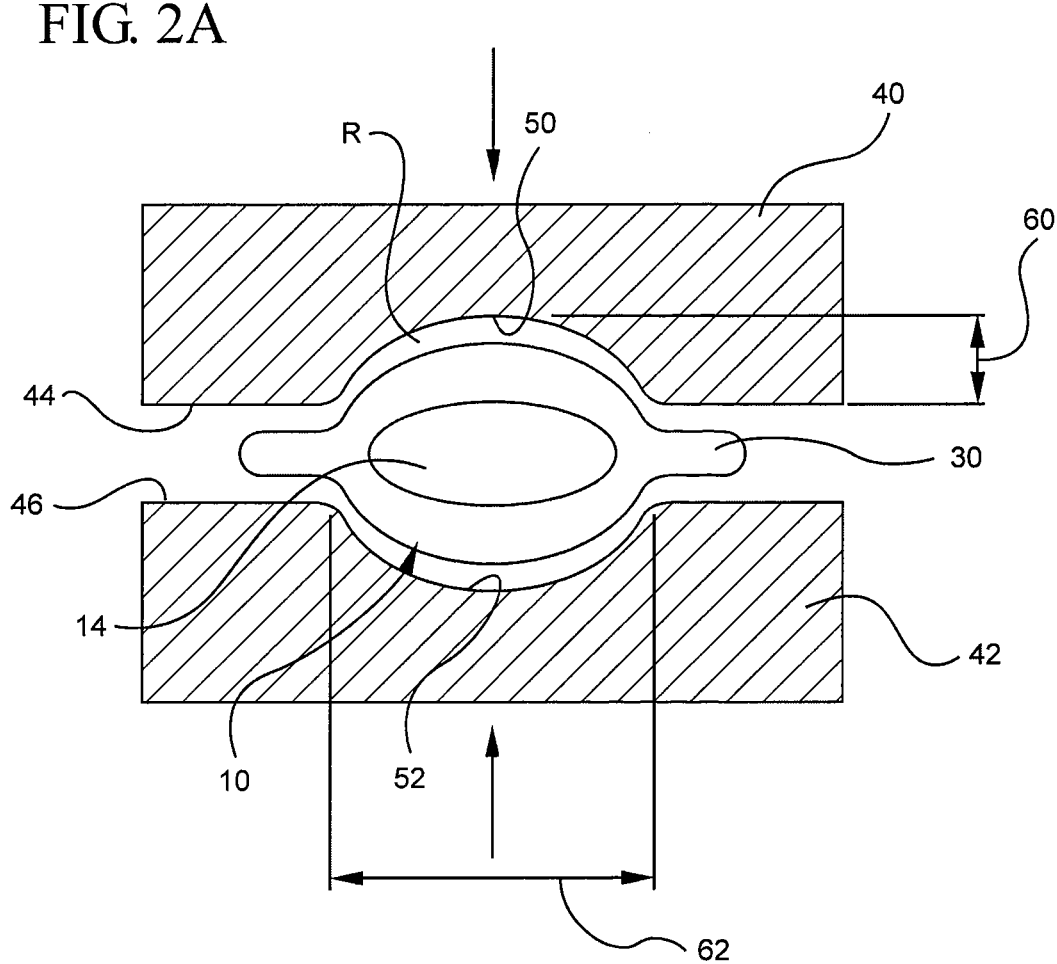
FIG. 2A is a cross-section view of a needle following a crimping method of the present invention.

Referring now to FIG. 2A, a representative embodiment of crimping method in accordance with the present invention is shown. Generally, crimping methods of the present invention are configured to provide a 30 feature on an outer surface 12 of a needle 10 without compromising a flow efficiency of the needle 10. For example, the needle 10 of FIGS. 2A and 2B have been crimped by a method of the present invention. The method by which the needle 10 of FIGS. 2A and 2B were crimped requires that an upper anvil 40 and a lower anvil 42 be modified over the prior art to include opposing, recessed surfaces 50 and 52, respectively. Opposing planar surfaces 44 and 46 have been modified over the prior art to include inwardly projecting recesses 50 and 52 having profiles that generally mirror the outer surface 12 of the needle 10. In some embodiments, the depth 60 of the recess 50 and/or 52 is selected to be greater than, or equal to one-half of the outer diameter of the needle 10. Additionally, in some embodiments the width 62 of the recess 50 and/or 52 is selected to be less than the outer diameter of the needle 10. As such, when the needle 10 is compressed, or pinched between the upper and lower anvils 40 and 42, the recessed portions 50 and 52 of the anvils 40 and 42 do not contact the outer surface 12 of the needle 10. Rather, the planar portions 44 and 46 of the anvils 40 and 42 contact the outer surface 12 of the needle 10 thereby pinching the outer surface 12 of the needle 10 proximal to the planar surfaces 44 and 46. For these embodiments, the process of crimping the needle 10 between the upper and lower anvils 40 and 42 generally preserves the cross-sectional profile of the inner lumen 14 of the needle 10. Additionally, the process of crimping the needle 10 pinches and outwardly extends a portion of the needle's outer surface 12 to provide a feature or crimp 30, again while preserving the cross-sectional profile of the inner lumen 14.

In some embodiments, the depth 60 of the recess 50 and/or 52 is selected to be less than one-half of the outer diameter of the needle 10. Additionally, in some embodiments the width 62 of the recess 50 and/or 52 is selected to be less than the outer diameter of the needle 10. As such, when the needle 10 is compressed, or pinched between the upper and lower anvils 40 and 42, the recessed portions 50 and 52 of the anvils 40 and 42 contact the outer surface 12 of the needle 10 to slightly compress the cross-sectional profile of the inner lumen 14. Although the inner lumen 14 is slightly compressed, the recessed surfaces 50 and 52 of the upper and lower anvils 40 and 42 prevent occlusion of the lumen 14 thereby preserving the flow efficiency of the needle 10. Additionally, the process of crimping the needle 10 pinches and outwardly extends a portion of the needle's outer surface 12 to provide a feature or crimp 30, as shown in FIGS. 2A and 2B.

Figure 2B:
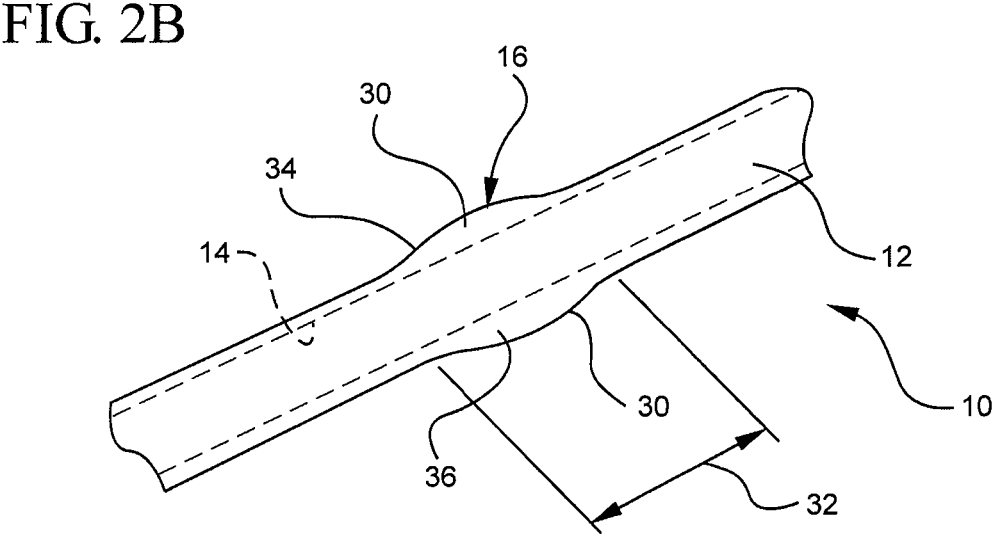
FIG. 2B is a perspective top view of a needle following a crimping method of the present invention.

Referring now to FIG. 2B, a perspective view of a crimped needle 10 is shown. The crimped portion 16 of the needle 10 may be configured to extend any length along the outer surface 12 of the needle 10. The length 32 of the feature 30 along the needle 10 is generally determined by the length of the upper and lower anvils 40 and 42. In some embodiments, the planar surfaces 44 and 46 of each anvil 40 and 42 is configured to provide a needle feature 30 that is compatible with a needle tip shield (not shown) or another needle safety device (not shown). For example, in some embodiments a needle feature is provided having a spiraled configuration. In other embodiments, a needle feature is provided having various configurations of height and width. Still further, in other embodiments an upper and lower anvil are used to provide a first needle feature occupying a first space on the outer surface of the needle, and a second needle feature occupying a second space. Other embodiments include providing a first needle feature having a first thickness, and providing a second needle feature having a second thickness. Finally, in some embodiments a plurality of alternating needle features is provided on the outer surface of the needle. In some embodiments, each alternating feature is oriented at approximately 90° to an adjacent alternating feature. In other embodiments, each alternating feature comprises a different profile or property to meet a specific need or provide a specific function.

In FIG. 2B, a single needle feature 30 is provided wherein a first portion 34 of the feature 30 occupies a first side of the needle 10 and a second portion 36 of the feature 30 occupies a second side of the needle 10. Each portion 34 and 36 of the feature 30 flanks the inner lumen 14 of the needle such that the feature 30 does not interfere with the flow efficiency of the needle 10.

Figure 3A:
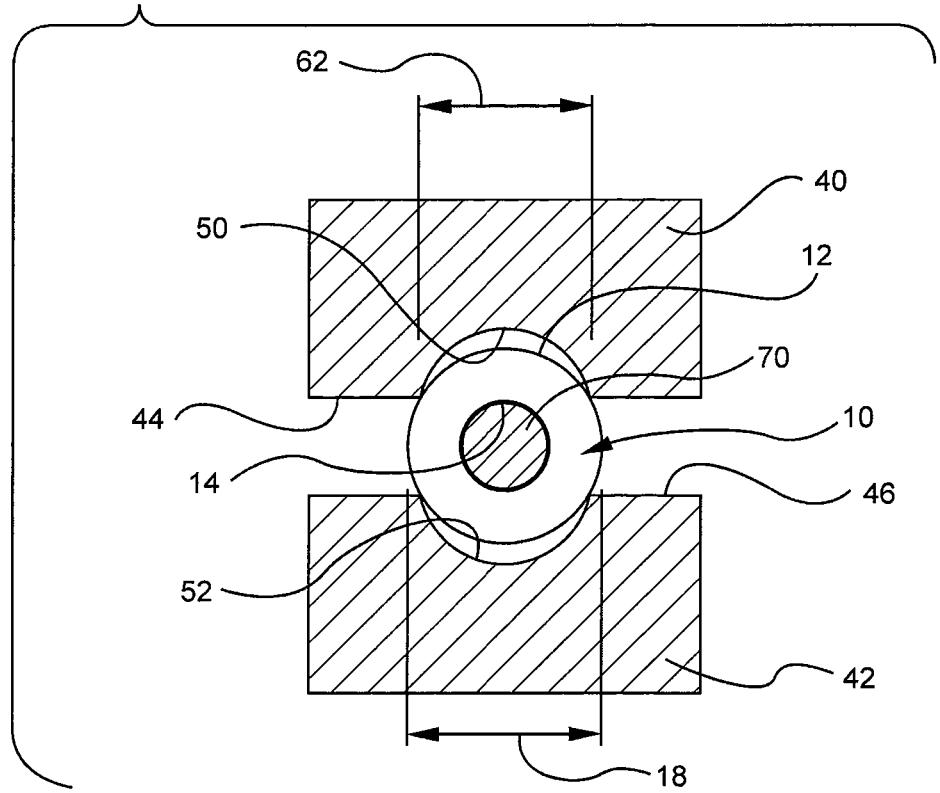
FIG. 3A is a cross-section view of a needle and inserted stylet prior to being crimped according to a crimping method of the present invention.

Referring now to FIG. 3A, a needle 10 is shown prior to being compressed between an upper anvil 40 and a lower anvil 42. In some embodiments of the present invention, a stylet or mandrel 70 is inserted into the inner lumen 14 of the needle 10 prior to compressing the needle 10. The mandrel 70 generally comprises a hardened or semi-hardened material that is capable of maintaining its cross-sectional shape under compression. The presence of the mandrel 70 within the inner lumen 14 of the needle 10 preserves the cross-sectional shape of the inner lumen 14 during compression of the needle 10. In some embodiments, the cross-sectional shape of the mandrel 70 is selected to be generally identical to the cross-sectional shape of the inner lumen 14.

In other embodiments, the cross-sectional shape of the mandrel 70 is selected to permit control reconfiguration of the cross-sectional shape of the inner lumen 14 during compression of the needle. For example, in some embodiments the cross-sectional shape of the mandrel 70 is elliptical. In other embodiments, the cross-sectional shape of the mandrel 70 is generally round yet comprises an outward extension or protrusion (not shown). As such, when the needle 10 is compressed between the upper and lower anvils 40 and 42, the outward protrusion prevents compression of a portion of the needle 10 thereby forming a feature on the outer surface 12 of the needle 10.

Figure 3B:
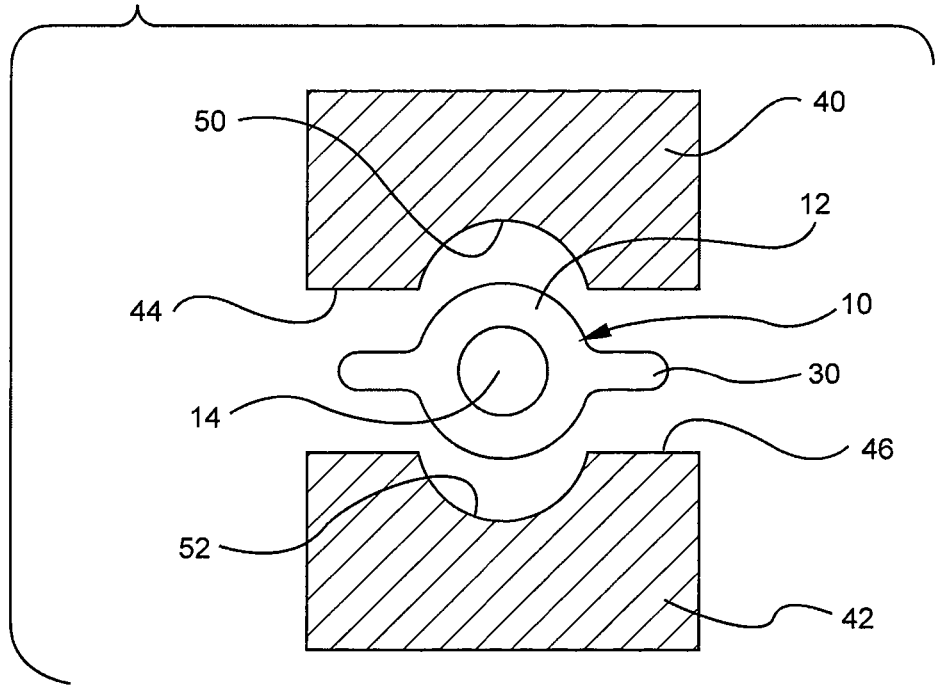
FIG. 3B is a cross-section view of a crimped needle having been crimped according to a crimping method of the present invention.

A feature 30 is formed as the upper and lower anvils 40 and 42 are drawn towards one another, thereby compressing the needle 10 within opposing recessed surfaces 50 and 52. In some embodiments, the width 62 of the recess 50 and/or 52 is configured to be less than the width or outer diameter 18 of the needle 10. As such, when the upper and lower anvils 40 and 42 are pressed together, opposing planar surfaces 44 and 46 contact and plastically deform the outer surface 12 of the needle 10 to provide a needle feature 30, as shown in FIG. 3B. Additionally, in some embodiments the width 62 of the recess 50 and/or 52 is configured to be less than the width of the outer diameter 18 of the needle, yet greater than the diameter of the inner lumen 14. Thus, when the upper and lower anvils 40 and 42 compress the needle 10, the outer surface 12 of the needle 10 is plastically deformed to provide a needle feature 30 while leaving sufficient material between the needle feature 30 and the inner lumen 14. In some embodiments, the combination of the recessed surfaces 50 and 52, and the inserted mandrel 70 preserve the cross-sectional shape of the inner lumen 14 of the needle 10 during the compression process.

Referring now to FIG. 3B, a needle 10 is shown following compression between the upper and lower anvils 40 and 42. Following formation of the needle feature 30 via plastic deformation of the outer surface 12 of the needle 10, the stylet or mandrel 70 is removed from the inner lumen 14 to reveal the preserved cross-sectional shape of the needle 10. In some embodiments, an outer surface of the mandrel 70 is coated with a lubricant prior to being inserted into the inner lumen 14 of the needle 10. As such, the lubricant assists in removal of the mandrel 70 following the compression process.

Figure 4:
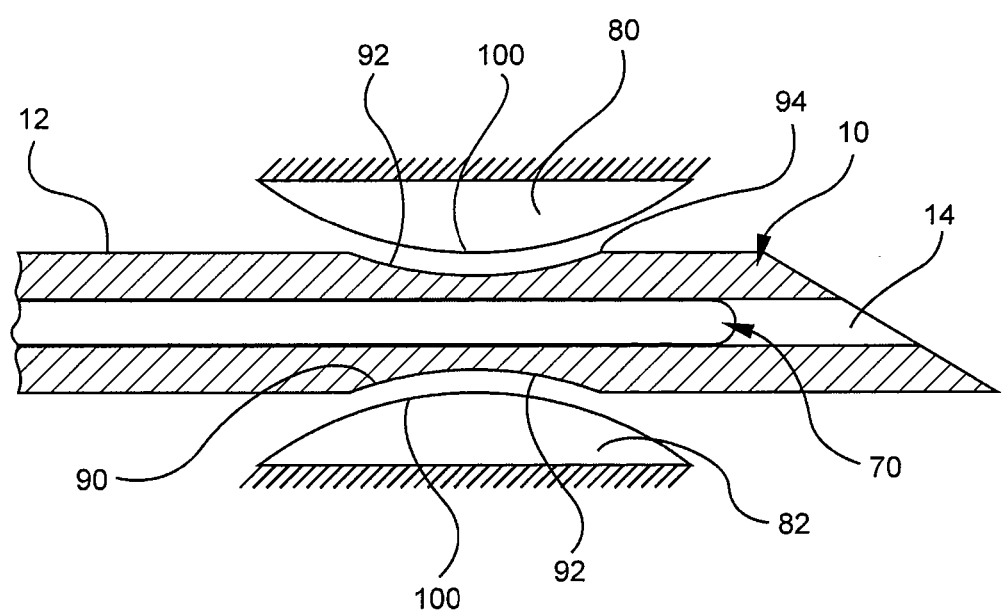
FIG. 4 is a cross-section view of a needle and inserted stylet following a crimping method of the present invention.

Referring now to FIG. 4, a needle 10 is shown following compression of a needle 10 between an upper anvil 80 and a lower anvil 82. In some embodiments of the present invention, a needle feature 90 is provided by pinching a portion of a needle 10 between opposing anvils 80 and 82, each anvil having a positively protruded contact surface 100. The protruded contact surface 100 generally comprises a rounded profile that is configured to strike the outer surface 12 of the needle 10 to provide a divot 92 in the outer surface 12 of the needle 10. One of skill in the art will appreciate that the protruded surface 100 may include any profile shape, including, but not limited to, spherical, square, rectangular, elliptical, triangular, polyhedral, concave, convex, parabolic, and combinations thereof.

In some embodiments, the divot 92 provides a negative or relief surface that comprises a needle feature 90. In other embodiments, the process of making the divot 92 displaces other portions of the outer surface 12 of the needle 10 to provide positive or outwardly protruding surfaces (not shown) that comprise a needle feature. Still further, in other embodiments the divot 92 provides an edge surface 94 that comprises a needle feature. For some methods, it is desirable to insert a mandrel 70 into the inner lumen 14 of the needle 10 prior to striking the needle 10 with the opposing anvils 80 and 82. In some embodiments, the mandrel 70 is positioned such that the mandrel 70 overlaps the portion of the needle 10 proximal to the upper and lower anvils 80 and 82. As such, upon striking the outer surface 12 of the needle 10 with the opposing anvils 80 and 82, the cross-sectional profile of the inner lumen 14 is preserved.

The methods of the present invention provide a variety of needle features on an outer surface of a needle, while generally preserving a cross-sectional profile on the needle's inner lumen. The methods of the present invention further permit the formation of multiple needle features having multiple shapes and dimensions as required by a user for a specific or general application. Accordingly, the methods of the present invention are adapted to provide useful, functional, and highly modifiable needle features on the outer surface of a needle.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method for creating a feature on a needle, the method comprising:
   providing a needle having a tube wall defined by an inner diameter and an outer diameter, the needle further having a length;
   inserting a stylet into a hollow interior of the needle;
   providing a lubricant between the stylet and the hollow interior of the needle;
   providing a crimping device having a first anvil and a second anvil, the first and second anvils having opposing planar crimping surfaces, an opposing portion of each planar crimping surface comprising a singular arched surface having a signal curve, wherein a maximum diameter of the singular arched surface is less than the outer diameter of the needle and greater than the inner diameter of the needle;
   aligning the needle within the singular arched surfaces of the first and second anvils such that a portion of a wall thickness of the needle overlaps the singular arched surfaces and a planar portion of the opposing planar crimping surfaces, the hollow interior of the needle being confined within the singular arched surfaces; and
   crimping an outer surface of the needle between the planar portions of the opposing planar crimping surfaces such that a sheared portion of the outer surface is displaced outwardly into a gap between the planar portion of the opposing planar crimping surfaces.

2. The method of claim 1, further comprising crimping the outer surface of the needle at a plurality of positions along the length of the needle.

3. The method of claim 1, further comprising crimping the outer surface of the needle in a spiraled configuration.

4. The method of claim 1, further comprising crimping the outer surface of the needle to provide a crimp having a plurality of heights.

5. The method of claim 1, further comprising at least three anvils.

6. The method of claim 1, further comprising removing the stylet from the needle following crimping of the outer surface of the needle.

7. The method of claim 2, further comprising crimping the outer surface of the needle to provide a first crimp in a first orientation, and a second crimp in a second orientation, wherein the second crimp is rotated approximately 90° from the first crimp.

8. The method of claim 2, further comprising crimping the outer surface of the needle to provide a first crimp having a first thickness, and a second crimp having a second thickness.

9. The method of claim 2, further comprising crimping the outer surface of the needle to provide a plurality of alternating crimps, wherein each alternating crimp is oriented at approximately 90° to an adjacent alternating crimp.

* * * * *